United States Patent [19]

Horike et al.

[11] Patent Number: 4,834,533
[45] Date of Patent: May 30, 1989

[54] MEASURING THE REFRACTIVE INDEX OF LIQUID

[75] Inventors: Masanori Horike, Tokyo; Yutaka Ebi; Michio Umezawa, both of Kawasaki, all of Japan

[73] Assignee: Ricoh Company, Ltd., Tokyo, Japan

[21] Appl. No.: 22,954

[22] Filed: Mar. 6, 1987

[30] Foreign Application Priority Data

Mar. 7, 1986 [JP] Japan .................................. 61-49647

[51] Int. Cl.$^4$ ..................... G01N 21/41; G01N 15/06
[52] U.S. Cl. ..................................... 356/133; 356/128; 250/573
[58] Field of Search ............... 356/133, 128, 135, 136; 250/358.1, 341, 339, 573, 576

[56] References Cited

U.S. PATENT DOCUMENTS

| | | | |
|---|---|---|---|
| 3,282,149 | 11/1966 | Shaw et al. ......................... | 356/131 |
| 3,850,528 | 11/1974 | DeBellis .............................. | 356/133 |
| 3,999,857 | 12/1976 | David et al. ..................... | 356/131 X |
| 4,660,974 | 4/1987 | Machler et al. ................ | 356/328 X |

Primary Examiner—Eugene R. LaRoche
Assistant Examiner—Nathan W. McCutcheon
Attorney, Agent, or Firm—Oblon, Fisher, Spivak, McClelland & Maier

[57] ABSTRACT

An apparatus for measuring the refractive index of liquid particularly suitable for use in an ink-jet printing system is provided. The apparatus includes a light emitting diode and a photodiode which are optically coupled by an optical fiber which in turn is partly immersed in a liquid to be measured. In one aspect, the wavelength of light emitted from the light emitting diode is so set to be outside a light absorption wavelength range of the liquid to be measured. In another aspect, provision is made of a temperature dependent resistor which changes its electrical resistance depending on the temperature of the liquid to be measured so as to vary the level of the driving current to be applied to the light emitting diode thereby varying the amount of light to be emitted.

4 Claims, 7 Drawing Sheets

OPTICAL FIBER IMMERSED TIME (hour)

MEASURING THE REFRACTIVE INDEX OF LIQUID

BACKGROUND OF THE INVENTION

1. Field of the Invention

This invention relates to an apparatus for measuring the refractive index of liquid, and, in particular, to an apparatus for measuring the refractive index of such liquid as ink, which contains a dye as dispersed therein, suitable for use in an ink-jet printer, for example.

2. Description of the Prior Art

Figure 12:
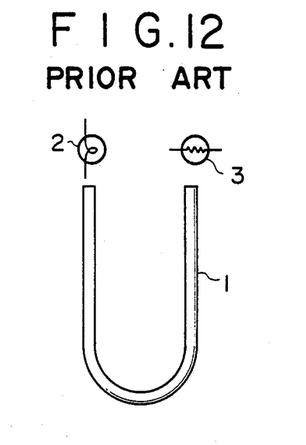
FIGS. 12 through 15 are schematic illustrations showing several prior art apparatuses for measuring the refractive index of liquid.

FIG. 12 shows a typical prior art apparatus for measuring the refractive index of liquid using a U-shaped optical fiber. As shown, the illustrated refractive index measuring apparatus includes a U-shaped optical fiber 1 having a light input end and a light output end, a light emitting element 2 located opposite to the light input end of the optical fiber 1, and a light receiving element 3 located opposite to the light outout end of the optical fiber 1. As is well known, in this apparatus, the curved portion of the U-shaped optical fiber 1 is immersed in a liquid whose refractive index is to be measured. In this case, the light emitted from the light emitting element 2 is introduced into the U-shaped optical fiber 1 through the light input end thereof, propagates through the optical fiber 1 and finally reaches the light receiving element 3. The amount of light which leaks out of the optical fiber 1 through its side surface varies depending on the refractive index of the liquid in contact with the optical fiber 1, so that the refractive index of the liquid in contact with the optical fiber 1 can be determined by measuring the amount of light emitted from the light output end of the optical fiber 1 by the light receiving element 3.

Figure 13:
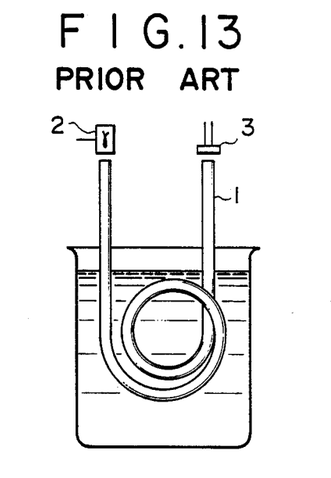
Figure 14:
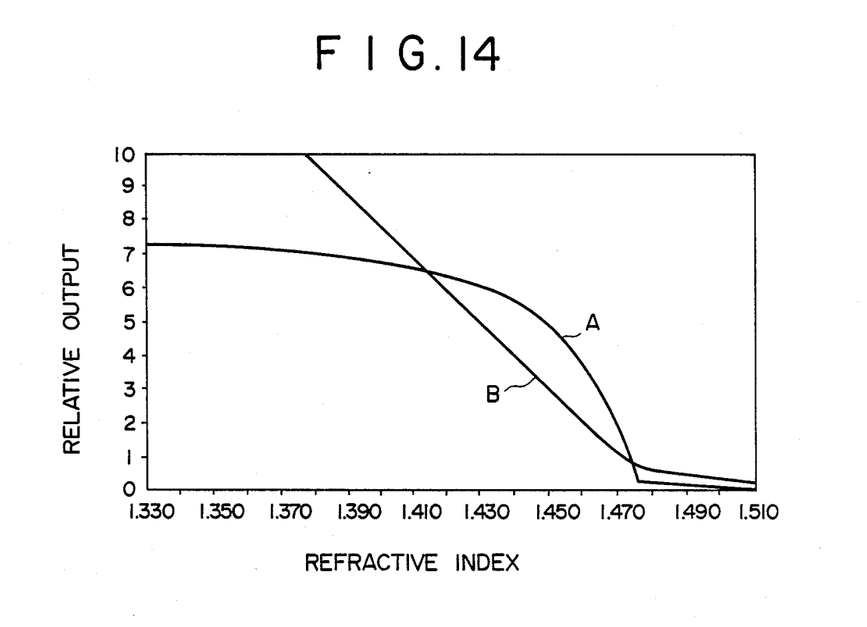

FIG. 13 shows another prior art apparatus for measuring the refractive index of liquid which is similar in structure to the apparatus shown in FIG. 12; however, in the apparatus shown in FIG. 13, the optical fiber 1 has a loop so as to improve the linearity in the characteristic. The structure shown in FIG. 13 is disclosed in the U.S. Pat. No. 3,282,149. FIG. 14 shows a graph which has its abscissa taken for the refractive index of liquid and its ordinate taken for the relative light output. In the graph of FIG. 14, the curve A indicates the output characteristic of the apparatus using the U-shaped optical fiber 1 shown in FIG. 12 and the curve B indicates the output characteristic of the apparatus using the loop shaped optical fiber 1 shown in FIG. 13. It is seen that the range of linearity in the output characteristic can be enlarged by using the loop-shaped optical fiber instead of the U-shaped optical fiber.

Figure 15:
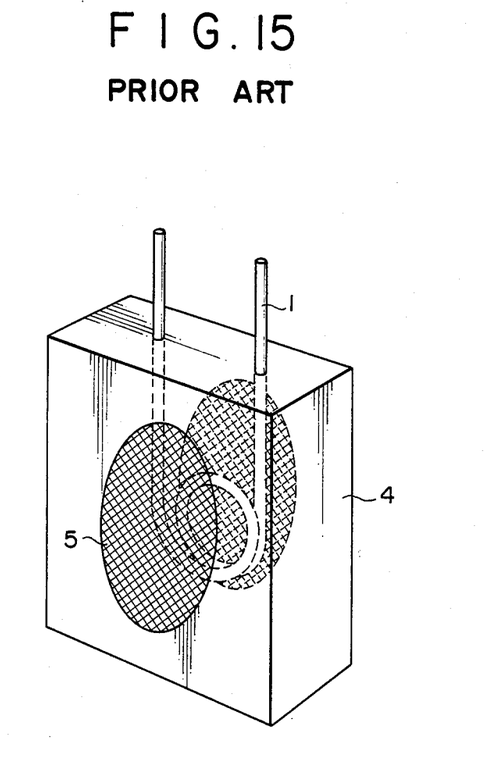

FIG. 15 shows a further prior art apparatus for measuring the refractive index of liquid which is disclosed in the Japanese Patent Laid-open Publication No. 56-73335. The apparatus shown in FIG. 15 is so structured to prevent the characteristic from deteriorating by the deposition of fine particles in the liquid to be measured onto the optical fiber 1. For this purpose, in the illustrated apparatus, the optical fiber 1 is enclosed in an enclosure 4, part of which is formed by a filter 5, thereby allowing the liquid to be measured to move into and out of the enclosure 4 freely, but to prevent fine particles and the like from entering into the interior of the enclosure 4. However, the structure shown in FIG. 15 tends to be bulky and is not effective for finer particles which pass through the filter 5. Besides, the characteristics of the light emitting and receiving elements vary depending on the disturbances in the abmient temperature, which constitute one of the factors for deteriorating the detection accuracy. It is to be noted that none of the prior art pays attention to the relation between the kind of liquid to be measured and the wavelength of a light source.

SUMMARY OF THE INVENTION

In accordance with one aspect of the present invention, there is provided an apparatus for measuring the refractive index of liquid, which comprises: light emitting means for emitting light; light receiving means for receiving light; light transmitting means for optically coupling said light emitting means and said light receiving means, said light transmitting means being partly immersed in a liquid to be measured, whereby the wavelength of the light emitted from said light emitting means is set outside the light absorption wavelength range of the liquid to be measured. In accordance with another aspect of the present invention, there is provided an apparatus for measuring the refractive index of liquid, which comprises: light emitting means for emitting light; light receiving means for receiving light; light transmitting means for optically coupling said light emitting means and said light receiving means, said light transmitting means being partly immersed in a liquid to be measured, and a liquid reservoir for storing therein a quantity of said liquid to be measured, whereby said light emitting and receiving means are both thermally coupled to said liquid reservoir.

It is therefore a primary object of the present invention to obviate the disadvantages of the prior art as described above and to provide an improved apparatus for measuring the refractive index of liquid.

Another object of the present invention is to provide an improved apparatus for measuring the refractive index of liquid with a suspension of particles or dye.

A further object of the present invention is to provide an improved apparatus for measuring the refractive index of liquid, which is not adversely affected by changes in the ambient temperature.

A still further object of the present invention is to provide an improved apparatus for measuring the refractive index of liquid at high accuracy at all times irrespective of the kind of the liquid to be measured.

A still further object of the present invention is to provide an improved apparatus for measuring the refractive index of liquid compact in size and reliable in operation.

Other objects, advantages and novel features of the present invention will become apparent from the following detailed description of the invention when considered in conjunction with the accompanying drawings.

DESCRIPTION OF THE PREFERRED EMBODIMENTS

Figure 1:
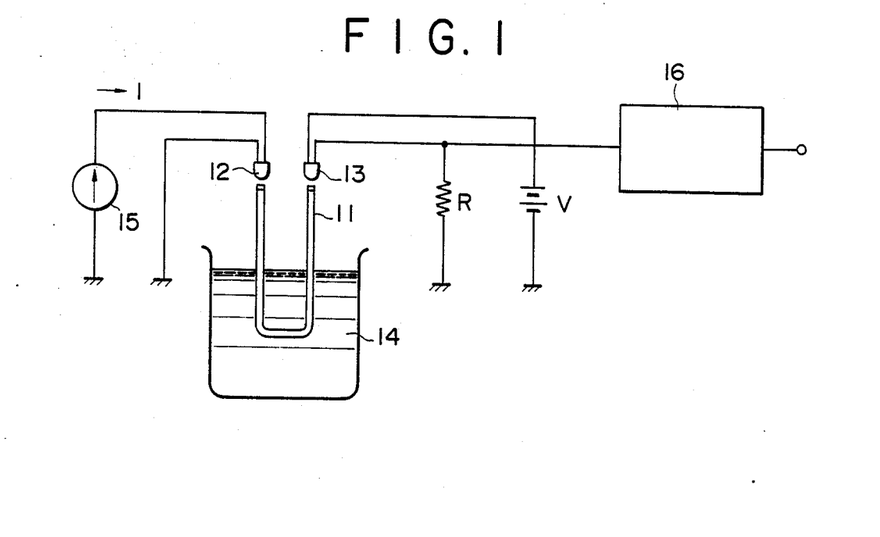
FIG. 1 is a schematic illustration showing an apparatus for measuring the refractive index of liquid constructed in accordance with one embodiment of the present invention.

Referring now to FIG. 1, there is shown an apparatus for measuring the refractive index of liquid constructed in accordance with one embodiment of the present invention. As shown, the illustrated apparatus includes a U-shaped optical fiber 11 having a light input end and a light output end, which is partly immersed in a liquid 14 to be measured, a light emitting element 12, such as a light emitting diode, located opposite to the light input end of the U-shaped optical fiber 11 and a light receiving element 13, such as a photodiode, located opposite to the light output end of the U-shaped optical fiber 11. The liquid 14 to be measured is stored in a reservoir. Also provided is a constant current source 15 which is electrically coupled to the light emitting element 12 to supply a constant current I. A detecting circuit 16 is also provided and it is electrically coupled to the light receiving element 13. A resistor R is connected between the junction between the detecting circuit and the light receiving element 13 and ground. A voltage source V is also connected between the light receiving element 13 and ground.

With this structure, the light transmitting along the longitudinal axis of the U-shaped optical fiber 11 partly leaks to the liquid 14 in contact with the optical fiber 11 and the amount of this leaking light differs depending on the refractive index of the liquid 14. Accordingly, the refractive index of the liquid 14 can be determined by detecting the amount of light received by the light receiving element 13. In this connection, if the entire optical fiber 11 is in contact with a medium having a small refractive index, such as air, the light inside of the optical fiber 11 is transmitted along the longitudinal axis of the optical fiber 11 through total reflection at the interface between the optical fiber 11 and the surrounding medium, and, thus, the output obtained at the photodiode 13 is relatively large. On the other hand, if the optical fiber 11 is immersed in the liquid 14 as shown in FIG. 1 and the liquid 14 has a refractive index similar to that of the optical fiber 11, the light transmitting along the optical fiber 11 tends to leak particularly at the curved portion of the optical fiber 11, so that the output level of the photodiode 13 tends to become lower. Therefore, designating the refractive index of the optical fiber 11 by $n_1$ and the refractive index of the liquid 14 by $n_2$, then the condition of $n_1$ being larger than $n_2$ must be satisfied, and the curvature of the optical fiber 11 must be appropriately set depending on the values of $n_1$ and $n_2$.

In the structure shown in FIG. 1, use is made of the light emitting diode 12 which is activated by the constant current I and the photodiode 13 to which a reversed bias of d.c. voltage V is applied. With this structure, the change of the current flowing through the photodiode 13 is detected as a change of the voltage across the resistor R. Thus, when the refractive index of the liquid 14 changes, the amount of leaking light from the optical fiber 11 changes, so that the detected voltage across the resistor R varies accordingly. Under the condition, if the liquid 14 is transparent and free of fine particles or the like, there arises no problem. However, in the case where the liquid 14 is not transparent because, for example, of inclusion of fine particles or the like, these particles or the like tend to be deposited onto the peripheral surface of the optical fiber 11, and, thus, the amount of leaking light from the optical fiber 11 changes constantly with time, which can be problematical.

Figure 2:
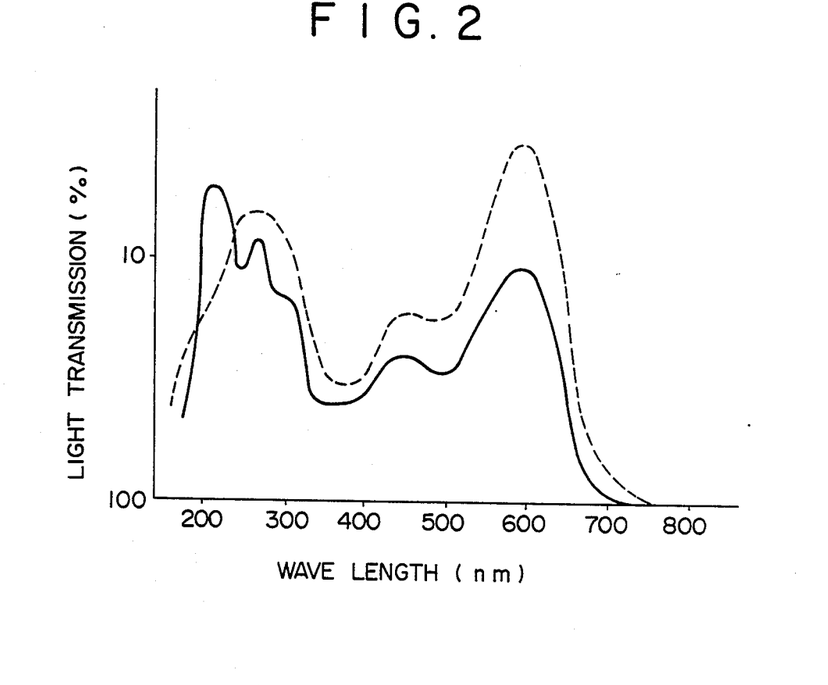
FIG. 2 is a graph showing the relation between the light transmission efficiency and the wavelength of light used.
Figure 3:
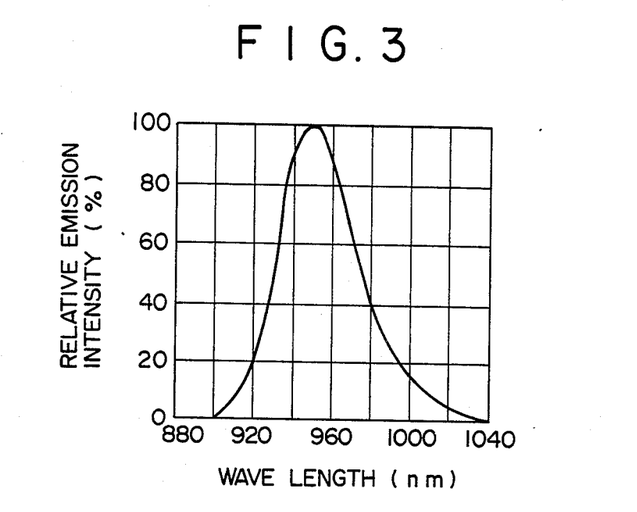
FIG. 3 is a graph showing the spectral distribution of the light emitted from a typical light emitting diode.

FIG. 2 shows a graph illustrating one example of the light transmission characteristic of a liquid as a function of the wavelength of the light. In general, the light transmission characteristic of a material resolved in the liquid, such as dye, indicates absorption for the light having the wavelength in the visible range, as shown in FIG. 2. For ink to be used in printing, the light having the wavelength in the infrared region of 750 nm or more is transmitted almost without absorption and the light transmission rate is 100%. On the other hand, FIG. 3 shows the spectral distribution of a typical infrared light emitting diode. As shown in FIG. 3, such light emitting diodes as GaAs or GaAlAs light emitting diodes emit the light having the wavelength in the infrared region of 900–1,000 nm. Accordingly, if use is made of such a light emitting diode as the light emitting element 12 of the present apparatus, the wavelength of the light to be transmitted through the optical fiber 11 can be set outside the absorption range of the liquid 14 with suspension. Thus, even if the suspended material, such as dye, is deposited onto the outer surface of the optical fiber 11, no deterioration in the detecting characteristic results by aging.

The above-described problem of deterioration by aging is more important for the case in which the optical fiber 11 is comprised of a resin material than the case in which the optical fiber 11 is comprised of a glass material. In the case where the optical fiber 11 is comprised of a resin material, such as methyl methacrylate or vinyl chloride, there is a chance that the fine particles, such as a dye, penetrate into the interior of the optical fiber 11. For this reason, the light transmitting characteristic of the optical fiber 11 is affected by these penetrated fine particles, which in turn would deteriorate the refractive index measuring capability.

The optical fiber 11 to be used in the present apparatus shown in FIG. 1 can be either of the clad type, in which case the optical fiber 11 includes a core and a clad surrounding the core, or of the non-clad type, in which case the optical fiber 11 is comprised of a single material. As described previously, if use is made of a silicon photodiode, whose peak in the spectral sensitivity resides in the range of 700-900 nm, as the light receiving element 13, it is particularly advantageous for the infrared light emitting diode 12.

Figure 4:
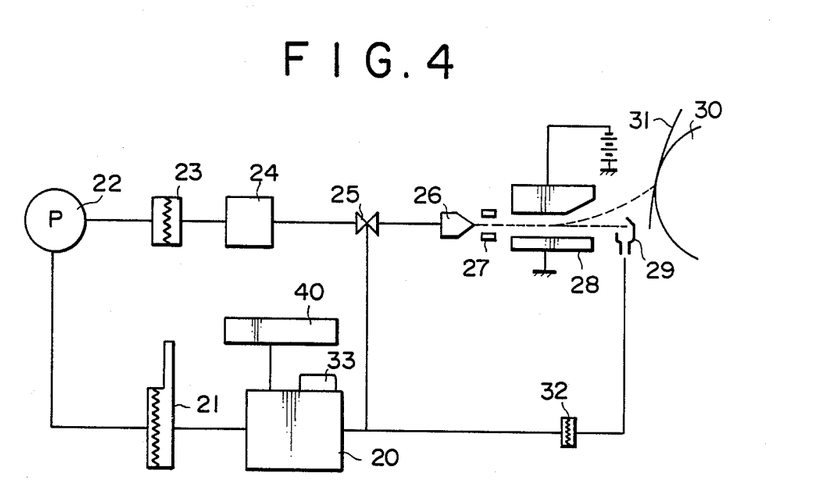
FIG. 4 is a schematic illustration showing an ink-jet printing system incorporating therein an apparatus for measuring the refractive index of liquid embodying the present invention.

FIG. 4 illustrates a charge controlling type ink-jet recording system to which the present invention has been applied. As shown, the system includes an ink tank 20 for storing therein a quantity of ink, a bubble catcher 21, a pump 22, a main filter 23, an accumulator 24, a valve 25, an ink-jet head 26, a charging electrode 27, a deflecting electrode assembly 28, a gutter 29, an ink filter 32, a new ink cartridge 33 and an evaporation rate detecting device 40 embodying the present invention. Also provided in the system is a platen roller 30 around which a sheet of recording paper 31 is placed. As well known in the art of an ink-jet printer, a series of ink droplets ejected out of the ink-jet head 26 is selectively charged by the charging electrode 27 in accordance with an image signal to be printed and then selectively deflected by the deflecting electrode assembly 28. Thus, the charged ink droplets are suitably deflected by the deflecting electrode assembly 28 and thus land on intended locations of the recording paper 31. On the other hand, those ink droplets which have not been sufficiently charged by the charging electrode 27 are not sufficiently deflected by the deflecting electrode assembly 28, so that these insufficiently charged or non-charged ink droplets are collected into the gutter 29. The ink droplets collected into the gutter 29 are transported to the ink tank 20 through the filter 32 for reuse. However, the ink changes its viscosity mainly due to evaporation of its liquid content while flying from the ink-jet head 26 to the gutter 29. There is an allowable limit for this change of ink viscosity due to evaporation of liquid content so as to maintain the quality of imprint, and, thus, the upper limit of this range must be detected and a correction must be carried out upon detection of the upper limit. For example, upon detection of the upper limit, part of the collected ink may be discarded and fresh ink is replenished, or a diluting liquid mainly composed of pure water is supplied by a predetermined amount into the system.

Figure 5:
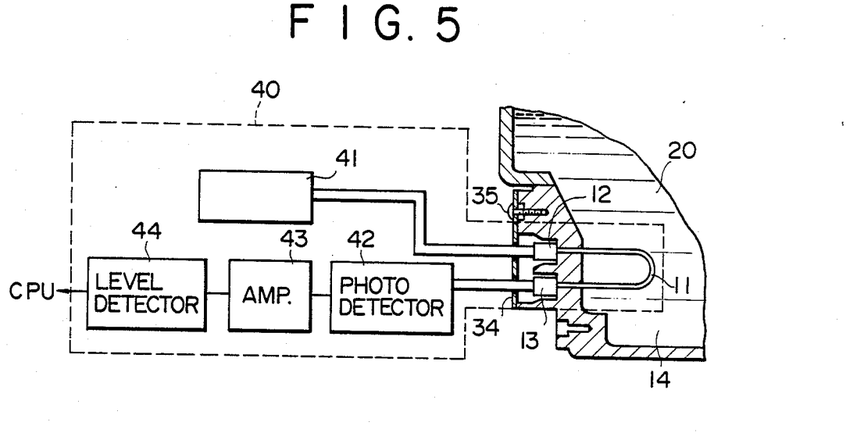
FIG. 5 is a schematic illustration showing in detail the ink tank and the evaporation rate detecting section provided in the system shown in FIG. 4.

FIG. 5 illustrates in detail the structure of the ink tank 20 and the evaporation rate detecting section 20 provided in the system of FIG. 4. The ink tank 20 stores therein a quantity of liquid ink 14. And, the ink tank 20 has a wall part of which defines as a support for supporting the U-shaped optical fiber 11 and a pair of the light emitting element 12 and the light receiving element, which are optically coupled to the U-shaped optical fiber 11. The U-shaped optical fiber 11 sticks out into the interior of the ink tank 20 with its light input and output ends located outside of the ink tank 20, and the light emitting and receiving elements 12 and 13 are mounted at the outside surface of the ink tank 20. Coupled to the light emitting element 12 is a constant current source 41 so that a constant current is supplied to the light emitting element 12 to cause the light emitting element 12 to emit a constant amount of light which is then introduced into the U-shaped optical fiber 11 through the light input end thereof. The light thus introduced into the U-shaped optical fiber 11 then propagates along the longitudinal axis of the optical fiber 11 and then impinges on the light receiving element 13 located to face the light output end of the optical fiber 11. The amount of light detected by the light receiving element 13 is processed through a photodetector 42, an amplifier 43 and a level detector 44 and then the processed output is supplied, for example, to a central processing unit CPU which controls the overall operation of the system shown in FIG. 4. In one embodiment, as mentioned previously, part of the wall defining the ink tank 20 is so shaped to have the light emitting and receiving elements 12 and 13 mounted thereon, and, upon placement of these elements 12 and 13 in position, they are preferably fixedly attached to the wall using a resin seal or an adhesive. Thus, these elements 12 and 13 are preferably integrally formed with the wall of the ink tank 20. Then, a printed circuit board 34, to which the terminals of these elements 12 and 13 are electrically connected, is placed on and fixed to the wall of the ink tank 20 by means of screws 35. The optical fiber 11, on the other hand, extends through mounting holes provided in the wall of the ink tank 20 and the gap between the optical fiber 11 and the mounting holes are filled with a filler, such as an adhesive agent.

Figure 6:
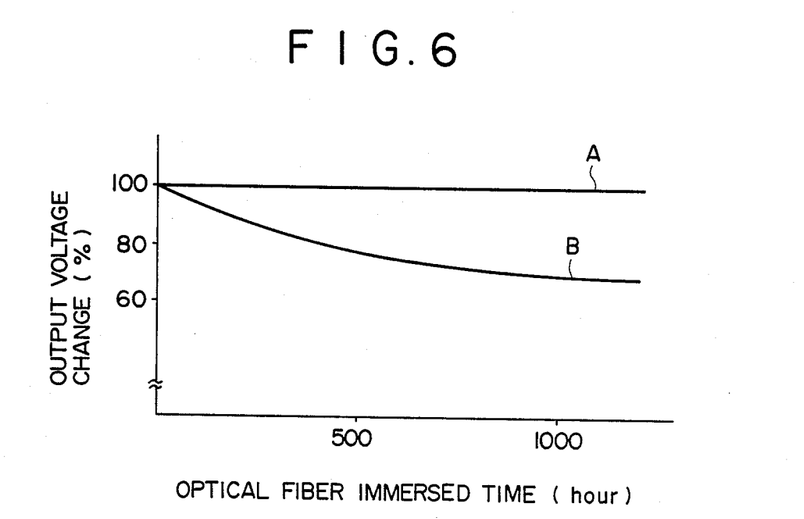
FIG. 6 is a graph showing the relation between the duration of immersion of the optical fiber in liquid and the output voltage change rate.

FIG. 6 is a graph showing the immersion durability characteristic of the optical fiber 11, in which the abscissa is taken for the duration in which the optical fiber 11 is immersed in a liquid to be measured and the ordinate is taken for the output voltage change in terms of %. In the graph of FIG. 6, the curve A is the case in which use is made of a light emitting diode which emits the light having the wavelength in the infrared region as the light emitting element 12. In this case, it is seen that there is no deterioration in characteristic by aging. On the other hand, the curve B is the case in which use is made of a light emitting diode which emits the light having the wavelength in the visible light region, e.g., 660 nm. In this case, it is seen that the amount of leaking light from the optical fiber 11 gradually increases and thus the output voltage gradually decreases by aging. It is to be noted that the liquid tested was an ink liquid containing coloring dye materials, such as cyan, magenta and yellow dye materials, and a black coloring dye material. It is thus clear that with the structure of the above-described embodiment, the refractive index of the non-transparent liquid, which contains a dye material or the like, can be determined accurately as well as reliably by using an extremely small optical fiber sensor.

Figure 7:
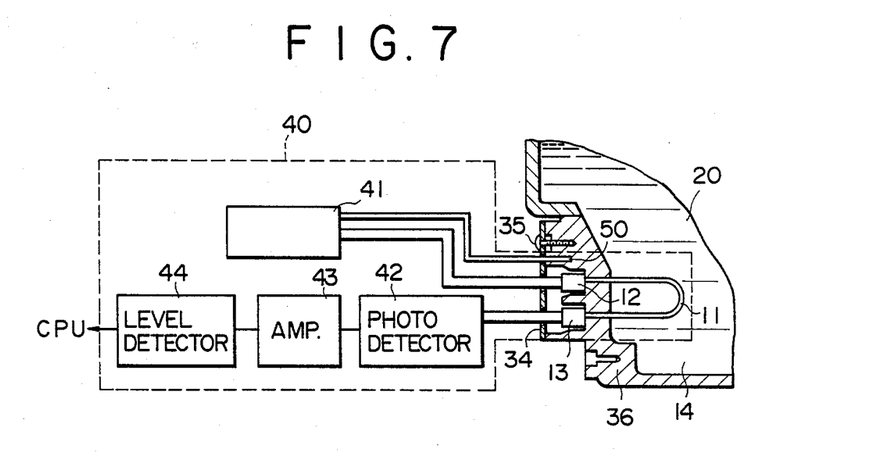
FIG. 7 is a schematic illustration showing in detail an alternative structure for the ink tank and the evaporation rate detecting section to be provided in the system shown in FIG. 4.

It should however be noted that even with the above-described apparatus for measuring the refractive index of a liquid, the characteristics of the light emitting and receiving elements 12 and 13 fluctuate depending on the level of the ambient temperature, so that the fluctuations of the ambient temperature could constitute an error in the output of the measuring apparatus. FIG. 7 illustrates another embodiment of the refractive index measuring apparatus addressed to solve such a problem arising from the fluctuations in the ambient temperature. It is to be noted that the apparatus shown in FIG. 7 is similar in many respects to the apparatus shown in FIG. 6, and, thus, like elements are indicated by like numerals with the omission of the repetition of description. The apparatus shown in FIG. 7, however, differs from the apparatus shown in FIG. 6 in the additional provision of a heat-sensitive element 50. As shown in FIG. 7, the heat-sensitive element 50 is embedded in the wall 36 of the ink tank 20 and, in the illustrated embodiment, located in the vicinity of the light emitting element 12. With this structure, the wall 36 of the ink tank 20 is substantially equal in temperature to the liquid 20 contained in the wall 36, and, thus, all of the light emitting and receiving elements 12 and 13 and the heat-sensitive element 50 are maintained substantially at the same temperature as that of the liquid 14 contained in the ink tank 20.

Figure 8:
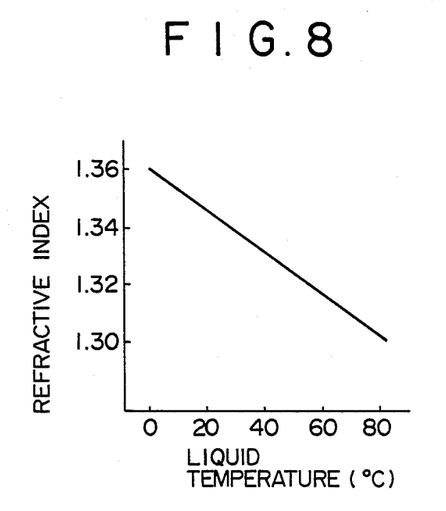
FIG. 8 is a graph showing the relation between the liquid temperature and the refractive index of liquid.
Figure 9:
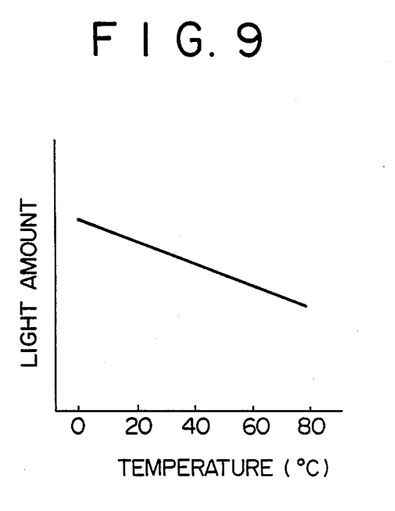
FIG. 9 is a graph showing the relation between the ambient temperature and the amount of light emitted from a typical light emitting diode.

FIG. 8 shows how the refractive index of the liquid 14 contained in the ink tank 20 varies as a function of the liquid temperature. As shown, the lower the liquid temperature, the higher the refractive index of the liquid 14. As described before, the refractive index $n_1$ of the optical fiber 11 and the refractive index $n_2$ of the liquid 14 to be measured must satisfy the inequality condition of $n_1$ being larger than $n_2$. However, as apparent from the graph of FIG. 8, at lower temperatures of the liquid 14, the refractive index $n_2$ becomes larger and approaches the value of $n_1$. For this reason, the amount of light leaking from the optical fiber 11 at the curved portion thereof to the surrounding increases, and, thus, the output current at the light receiving element 12 decreases. FIG. 9 is a graph showing how the amount of light emitted from a light emitting diode varies as a function of the ambient temperature. As shown, in general, the lower the ambient temperature is, the larger the amount of light emitted from a light emitting diode is. It is to be noted, however, that the values of the amount of light emitted differ depending on the kind of light emitting diodes. Of importance, the dependency of the light amount characteristic of a light emitting diode on the ambient temperature shown in FIG. 9 is opposite to the dependency of the refractive index characteristic of a liquid on the temperature shown in FIG. 8, and, thus, these two characteristics tend to cancel each other. It is also worth noting the fact that the temperature characteristic of a planer diffusion type photodiode is such that it exhibits a positive temperature coefficient in a large wavelength region of 700 nm or more and a negative temperature coefficient in a short wavelength region.

Figure 10:
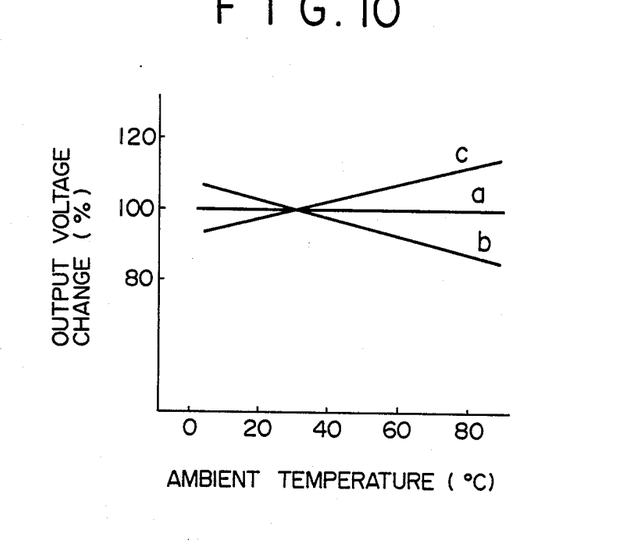
FIG. 10 is a graph showing the overall characteristics of the present detecting device in terms of a relation between the output voltage change rate and the ambient temperature.

Under the circumstances, the overall temperature characteristic of a detecting unit as a whole has three cases a, b and c as shown in FIG. 10 depending on the temperature characteristic of various factors including the liquid to be measured, light emitting diode, photodiode, or the like, and the current amplified output of a photodiode may be either positive or negative. However, by providing an integrated structure as shown in FIG. 7, all of the liquid, light emitting diode and photodiode can be maintained substantially at the same temperature. For example, as in the case of an ink-jet printing system even if the ambient temperature is substantially at constant, the circulating ink gradually increases its temperature after power up due, for example, to heating by a pump or the like. Under this condition, the temperature of each of the light emitting diode and photodiode also changes at the same rate so that the overall characteristic may be maintained at constant at all times in the case where the relation a shown in FIG. 10 holds. On the other hand, if the overall structure of the detecting unit has an integrated characteristic shown by either b or c in FIG. 10, then use is made of the heat-sensitive sensor 50 as shown in FIG. 7. For example, a nickel family resistor includes a resistor having a positive temperature coefficient in a range between 1,000 and 4,000 ppm.

Figure 11:
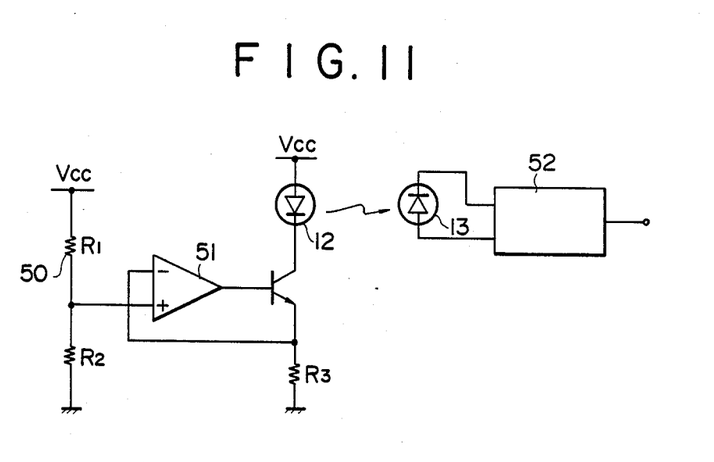
FIG. 11 is a circuit diagram showing one embodiment of the present detecting device.

FIG. 11 illustrates a circuit for correcting fluctuations resulting from the temperature dependent characteristic shown by either b or c in FIG. 10. For example, in the case where the characteristic c holds, a heat-sensitive resistor R1, such as a thermister, is provided in series with a resistor R2. With this structure, a reference voltage applied to the non-inverting input terminal of an operational amplifier 51 is automatically adjusted depending on the ambient temperature such that it decreases at lower temperature and increases at higher temperature. The flow of current is detected by a resistor R3, and it is controlled such that the current flowing through the light emitting diode 12 decreases to reduce the amount of light emitted from the light emitting diode 12 as the ambient temperature decreases; on the other hand, the amount of light emitted from the light emitting diode 12 increases as the ambient temperature increases, whereby the characteristic b may be suitably corrected. Alternatively, in the case where the characteristic c holds, the temperature dependency may be corrected by using a temperature-sensitive resistor for each of the resistors R1, R2 and R3 in the circuit of FIG. 11. In this manner, that component of the change of refractive index which depends on the ambient temperature can be suitably eliminated, and, thus, that component of the change of refractive index which depends on evaporation of water from the liquid or ink as in the case of a ink-jet printing system can be detected, thereby allowing to carry out correction at high accuracy.

As described above, in accordance with the present invention, measurements of the refractive index of a non-transparent liquid, such as a liquid with a suspension of a dye material, can be carried out using an extremely compact optical fiber sensor at high accuracy and high reliability. Besides, the present apparatus is capable of carrying out measurements without being significantly affected by the ambient temperature.

While the above provides a full and complete disclosure of the preferred embodiments of the present invention, various modifications, alternate constructions and equivalents may be employed without departing from the true spirit and scope of the invention. Therefore, the above description and illustration should not be construed as limiting the scope of the invention, which is defined by the appended claims.

What is claimed is:

1. Apparatus for measuring a refractive index of a liquid, comprising:
   means for emitting light having a predetermined wavelength;
   means for transmitting light having a light input end for receiving the light emitted from said emitting means and a light output end for outputting the light transmitted therethrough, said means for transmitting being partly immersed in a liquid to be measured, said liquid containing therein a suspension of a dye material having a first light absorption wavelength range to which said predetermined wavelength of the light emitted from said means for emitting does not belong;
   means for receiving the light output from the light output end of said means for transmitting, said means for receiving having a sensitivity to said predetermined wavelength of the light emitted from said means for emitting;
   monitoring means for monitoring an output from said means for receiving; and
   whereby said predetermined wavelength of the light emitted from said means for emitting is outside a second light absorption wavelength range of said liquid.

2. Apparatus of claim 1 wherein said means for emitting includes a light emitting diode which emits the light having a wavelength in an infrared region.

3. Apparatus of claim 1 wherein said means for receiving includes a silicon photodiode.

4. Apparatus of claim 1 wherein said liquid is an ink containing therein a suspension of said dye material, said means for emitting includes a light emitting diode which emits light having an infrared wavelength as said predetermined wavelength larger than said first light absorption wavelength range of said dye material, and said means for receiving includes a silicon photodiode having sensitivity to said infrared wavelength.

* * * * *